(12) United States Patent
Dalzell

(10) Patent No.: US 7,402,826 B2
(45) Date of Patent: Jul. 22, 2008

(54) SYSTEM AND METHOD FOR NON-DESTRUCTIVELY DETERMINING THICKNESS AND UNIFORMITY OF ANTI-TAMPER COATINGS

(75) Inventor: William J. Dalzell, Parrish, FL (US)

(73) Assignee: Honeywell International Inc., Morristown, NJ (US)

( * ) Notice: Subject to any disclaimer, the term of this patent is extended or adjusted under 35 U.S.C. 154(b) by 434 days.

(21) Appl. No.: 11/128,500

(22) Filed: May 13, 2005

(65) Prior Publication Data

US 2006/0255265 A1   Nov. 16, 2006

(51) Int. Cl.
*G01N 21/86*   (2006.01)
(52) U.S. Cl. ............................... 250/559.27; 250/559.4
(58) Field of Classification Search ............ 250/559.27, 250/559.4, 221, 201.1; 356/355, 381, 357
See application file for complete search history.

(56) References Cited

U.S. PATENT DOCUMENTS

| | | | | |
|---|---|---|---|---|
| 4,079,237 A | * | 3/1978 | Schlesinger | ................. 702/172 |
| 4,155,009 A | | 5/1979 | Lieber et al. | |
| 4,424,445 A | | 1/1984 | Joffe et al. | |
| 4,771,173 A | * | 9/1988 | Weismuller | ................. 250/308 |
| 5,369,299 A | | 11/1994 | Byrne | |
| 5,696,583 A | * | 12/1997 | Yoon | ........................... 356/497 |
| 5,877,093 A | | 3/1999 | Heffner et al. | |
| 6,013,318 A | | 1/2000 | Hunt et al. | |
| 6,287,985 B1 | | 9/2001 | Heffner et al. | |
| 6,319,740 B1 | | 11/2001 | Heffner et al. | |

FOREIGN PATENT DOCUMENTS

| | | |
|---|---|---|
| FR | 2087500 | 12/1971 |
| GB | 1463363 | 2/1977 |

OTHER PUBLICATIONS

ASTM International Standard Test Method for Measurement of Coating Thickness by the Beta Backscatter Method, ASTM—Designation: B 567-98, Jan. 1999, pp. 1-9, Publisher: ASTM International, Published in: US.
CMI International Inc. , Measuring Coating Thickness, p. 5, Publisher: PF Online, http://www.pfonline.com/article print1.cfm.

* cited by examiner

*Primary Examiner*—Que T Le
(74) *Attorney, Agent, or Firm*—McDonnell Boehnen Hulbert & Berghoff LLP

(57) ABSTRACT

An improved system and method are disclosed for non-destructively determining the thickness and uniformity of an anti-tamper coating on a sensitive electronic part, such as, for example, an integrated circuit, multi-chip module, or other type of electronic device, component or equipment. The system includes an anti-tamper coating thickness measurement probe with a highly collimated beta radiation source and a Geiger-Muller tube sensitive to beta radiation arranged in close proximity to the beta radiation source. The probe is placed on or in close proximity to the anti-tamper coating on the part, so that the beta radiation electrons penetrate the coating material and are reflected back (back scattered) toward the beta radiation source and the Geiger-Muller tube. The Geiger-Muller tube collects the electrons from the back scattered radiation.

17 Claims, 1 Drawing Sheet

US 7,402,826 B2

1

SYSTEM AND METHOD FOR NON-DESTRUCTIVELY DETERMINING THICKNESS AND UNIFORMITY OF ANTI-TAMPER COATINGS

FIELD OF THE INVENTION

The present invention relates generally to the non-destructive testing field, and more specifically, but not exclusively, to an improved system and method for non-destructively determining the thickness and uniformity of anti-tamper coatings applied to electronic parts.

BACKGROUND OF THE INVENTION

The need to protect sensitive electronic circuits, components or equipment against unauthorized access is well known. For example, electronic circuits, components and systems used in military weapons or other fielded military equipment can contain classified structures or data that needs to be protected against unauthorized access. Notably, the strategic, tactical or operational value of the classified structures or data that may be compromised by such unauthorized access is unquantifiable. Also, the ability to protect such sensitive electronic circuits, component or systems against unauthorized access is weakened if the sensitive electronic circuits, components or systems are not under domestic control (e.g., foreign military sales of classified weapon systems).

Similarly, electronic circuits, components or systems used for civilian applications can contain sensitive, proprietary information that needs to be protected against unauthorized access. For example, financial institutions and corporations use computerized systems to protect sensitive information (e.g., personal data, customer data, financial data, financial transaction authorization codes, authentication procedures, security passwords, etc.). Such sensitive information may be stored in alterable semiconductor memory devices (e.g., flash memory device, EPROM, EEPROM, PROM, RAM, DRAM, etc.) or memory components of integrated circuits. Any compromise in the security of the sensitive data contained in such memory devices or integrated circuits can result in significant tangible and intangible losses to the financial institutions and corporations involved, such as, for example, financial losses, losses due to fraudulent transactions, business losses, losses due to compromised customer lists and financial data, losses of institutional or corporate integrity, losses of commercial confidence, and losses due to adverse publicity. Thus, electronic circuits, components or systems containing sensitive information used for civilian applications also need to be protected against unauthorized access.

One technique for protecting sensitive hardware and software devices is discussed in commonly-assigned U.S. Pat. No. 5,877,093 to Heffner et al., entitled "Process For Coating An Integrated Circuit Device With A Molten Spray." Heffner et al. disclose forming a primer coating and an opaque coating on an integrated circuit or multi-chip module. A primer coating composition is applied to a surface of the integrated circuit device or multi-chip module. An opaque coating composition is then applied over the primer coating to form an opaque coating that overlies the active circuitry on the surface, in order to prevent optical- and radiation-based inspection and reverse engineering of the active circuitry. Other related coating techniques for protecting sensitive hardware and software devices are discussed in commonly-assigned U.S. Pat. No. 6,287,985 to Heffner et al., entitled "Process For Applying A Molten Droplet Coating For Integrated Circuits," and commonly-assigned U.S. Pat. No. 6,319,740 to Heffner et al., entitled "Multilayer Protective Coating For Integrated Circuits And Multi-chip Modules And Method Of Applying Same." Notably, such protective coatings for sensitive hardware and software devices are referred to as anti-tamper coatings.

A significant problem with existing anti-tamper coating techniques is that the coatings are highly complicated structures, which are designed to thwart an intruder's physical or electronic attempts to access the active circuitry underneath (e.g., by drilling through or removing the coating, and/or optically or electronically detecting the structure of the active circuitry underneath). Consequently, it is a very complicated, time consuming, and expensive process to evaluate the quality of an anti-tamper coating on a part, or test and evaluate the performance of such an anti-tamper coated part. For example, if a number of anti-tamper coated parts are produced for a classified, government application, then these parts can be shipped to an authorized government facility for specialized evaluation and testing. However, the specialized testing and shipping of these parts are very time consuming and expensive processes, and the tested parts are typically destroyed or made useless as a result. As another example, each anti-tamper coated part can be tested individually to determine if the coating has damaged that part. Again, these tests are very time consuming and performed with expensive, specialized equipment, and the tested parts are typically destroyed or made useless as a result. Therefore, it would be advantageous to provide an improved system and method for non-destructively testing and evaluating anti-tamper coatings on sensitive electronic parts, which use inexpensive processes that take relatively little time to perform. As such, one non-destructive technique that can be used to determine the performance of the constituent elements in an anti-tamper coating material and thus the performance of the anti-tamper coating itself, is to measure the thickness and uniformity of the anti-tamper coating on the part. As described in detail below, the present invention provides such an improved system and method, which can be used to non-destructively determine the thickness and/or uniformity of an anti-tamper coating material on a sensitive electronic part.

SUMMARY OF THE INVENTION

The present invention provides an improved system and method for non-destructively determining the thickness and uniformity of an anti-tamper coating on a sensitive electronic part, such as, for example, an integrated circuit, multi-chip module, or other type of electronic device, component, system or equipment. In accordance with a preferred embodiment of the present invention, a system for non-destructively determining the thickness and uniformity of an anti-tamper coating on a part is provided, which includes a source unit for emitting beta radiation, a detection unit for collecting electrons associated with beta radiation reflected from an anti-tamper coating material on an electronic part, a meter unit associated with the detection unit for counting or quantifying the collected electrons, and a conversion unit for converting a first value associated with an electron count received from the meter unit to a second value associated with a thickness of the anti-tamper coating material on the electronic part. For one example embodiment, an anti-tamper coating thickness measurement probe is provided, which includes a highly collimated beta radiation source and a Geiger-Müller tube (e.g., "Geiger Counter") sensitive to beta radiation arranged in close proximity to the beta radiation source. The probe is placed on or in close proximity to the anti-tamper coating on the part, so that the beta radiation electrons penetrate the coating material and are reflected back (back scattered) toward the beta radiation source and the Geiger-Müller tube. The Geiger-Müller tube collects the electrons from the back scattered (reflected) radiation, a rate meter associated with the Geiger-Müller tube counts or quantifies the collected electrons, and a conversion unit converts the electron count value of the back scattered radiation to a thickness value for the anti-tamper coating. The uniformity of the anti-tamper coating can be determined by performing such thickness tests at multiple locations on the coated part. Thus, the present invention provides an approach that can be used to determine the thickness and uniformity of an anti-tamper coating on a sensitive electronic part, without affecting the performance and quality of the anti-tamper coating or the part.

BRIEF DESCRIPTION OF THE DRAWINGS

The novel features believed characteristic of the invention are set forth in the appended claims. The invention itself, however, as well as a preferred mode of use, further objectives and advantages thereof, will best be understood by reference to the following detailed description of an illustrative embodiment when read in conjunction with the accompanying drawings, wherein:

DETAILED DESCRIPTION OF PREFERRED EMBODIMENT

Figure 1:
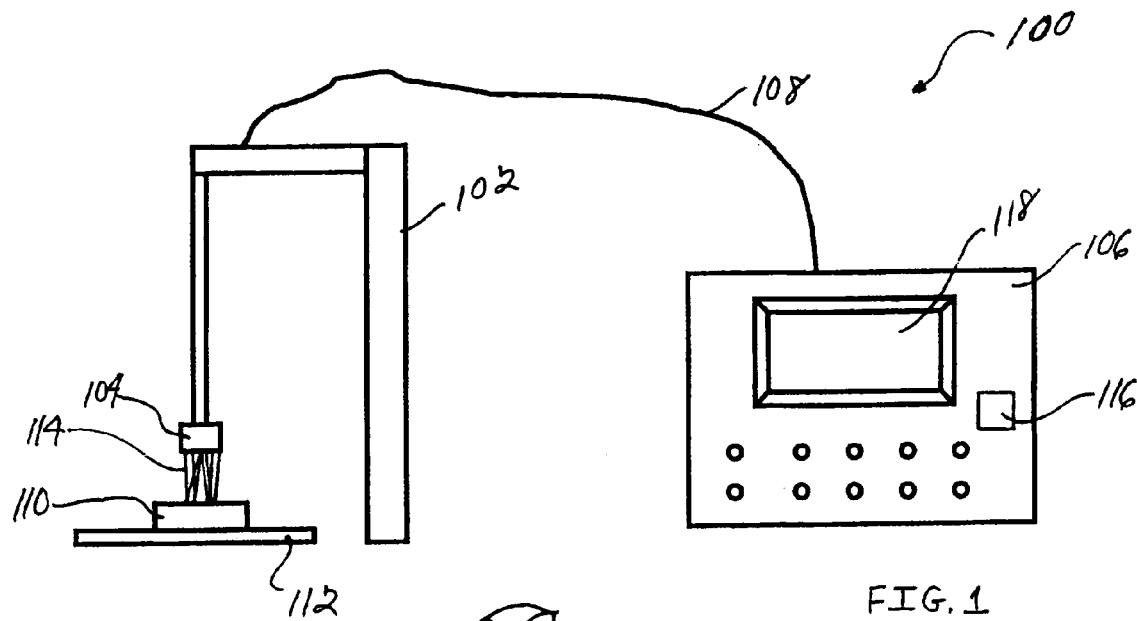
FIG. 1 depicts a pictorial representation of an example system for non-destructively determining the thickness and uniformity of an anti-tamper coating on a part, which can be used to implement a preferred embodiment of the present invention.

With reference now to the figures, FIG. 1 depicts a pictorial representation of an example system 100 for non-destructively determining the thickness and uniformity of an anti-tamper coating on a part, which can be used to implement a preferred embodiment of the present invention. For this example embodiment, system 100 includes a test stand 102, a test probe unit 104 connected to and supported by test stand 102, a test measurement and display unit 106, and a conductor 108 for electrically coupling test probe unit 104 to test measurement and display unit 106. A part 110 to be tested (e.g., electronic circuit, integrated circuit, semiconductor chip, multi-chip module, component, system, etc.), which is coated with an anti-tamper coating material, is supported on a test base unit 112. Also, for illustrative purposes, a plurality of radiated and reflected (e.g., back scattered) rays are represented by and identified as element(s) 114. Preferably, but not a limitation to be imposed on the scope of the present invention, the atomic number of the primary constituent material(s) in the anti-tamper coating is selected to be sufficiently different (e.g., at least four atomic numbers) from the atomic number of the constituent element(s) in the tested part.

Figure 2:
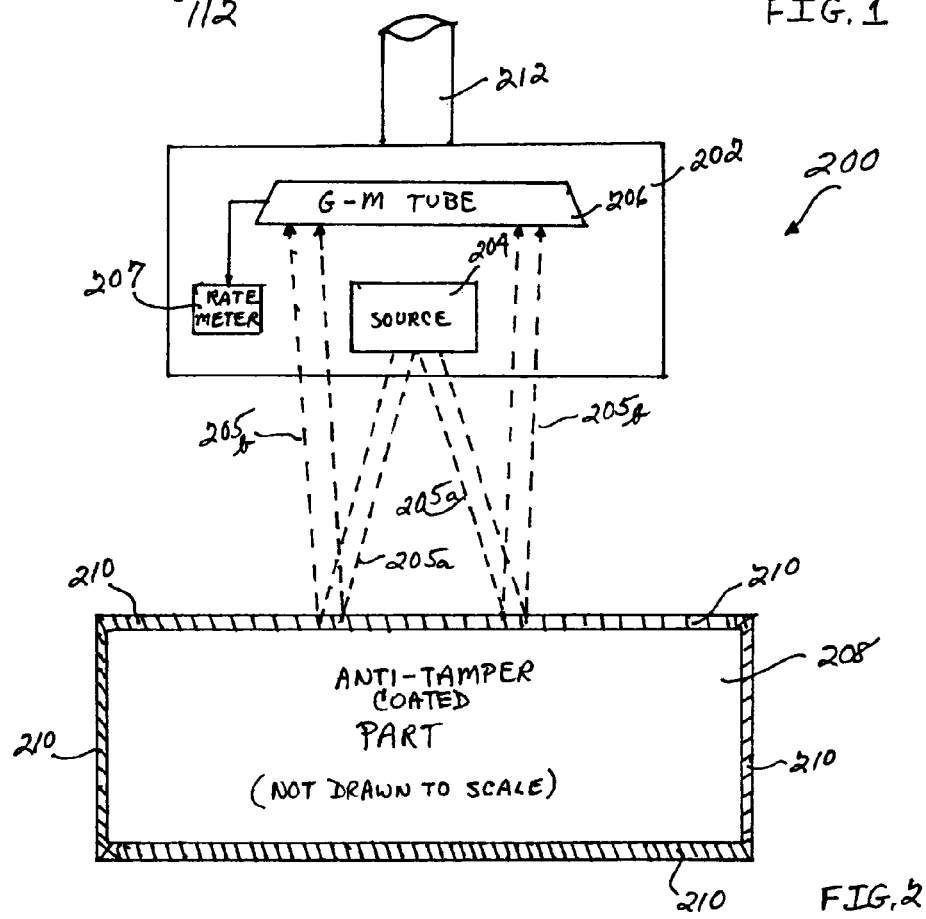
FIG. 2 depicts a pictorial representation of an example test arrangement, which is provided to illustrate principles of the present invention with further details of the probe unit and anti-tamper coated part shown in the example embodiment of FIG. 1.

FIG. 2 depicts a pictorial representation of an example test arrangement 200, which is provided to illustrate principles of the present invention with further details of probe unit 104 and anti-tamper coated part 110 shown in the example embodiment of FIG. 1. Referring now to FIGS. 1 and 2 for this example embodiment, a test probe 202 (e.g., test probe unit 104 in FIG. 1) includes a radiation source 204 for emitting beta radiation (e.g., exemplified by dashed lines 205a), a detection unit 206 (e.g., Geiger-Müller tube) for collecting electrons associated with beta radiation 205b reflected back (back scattered) from an anti-tamper coating material 210 on an electronic part 208, and a rate meter 207 coupled to detection unit 206 for counting or quantifying a number of electrons collected over a predetermined period of time. For this example, a pertinent section 212 of a test stand is provided for illustrative purposes and also to be consistent with the example shown in FIG. 1. Also, rate meter 207 can be located internally or externally (e.g., in test and measurement unit 106) with respect to test probe 202. However, it should be understood that although test probe 202 (and test probe unit 104 in FIG. 1) are shown supported by a test stand in this illustrative example, the present invention is not intended to be so limited and can also include the use of a portable, hand-held test probe for test probe 202.

An output signal (e.g., a value represented as electron counts per minute) from rate meter 207 can be coupled to an input of a test measurement and display unit (e.g., test measurement and display unit 106) via conductor 108 in FIG. 1. For this example embodiment, test measurement and display unit 106 in FIG. 1 includes a conversion unit 116 (e.g., digital processor in test measurement and display unit 106 operable to execute a suitable algorithm implemented in software) for converting the first value associated with the electron count signal received from rate meter 207 to a second value representing a thickness of the tested portion of the anti-tamper coating material 210 on the electronic part 208. The second value representing thickness can be displayed, for example, on a screen 118 of test measurement and display unit 106.

Notably, although the example embodiment illustrated in FIGS. 1 and 2 depicts test probe unit 104 (or test probe 202) and test measurement and display unit 106 as separate components, a second embodiment of the invention can be implemented, for example, with a single anti-tamper coating thickness (and uniformity) test and measurement device or system, including a test probe unit (e.g., such as test probe unit 104 implemented as test probe 202 in FIG. 2), a conversion unit for converting the first value associated with the electron count signal received from a rate meter to a second value representing a thickness of the tested portion of the anti-tamper coating material on the electronic part (e.g., such as conversion unit 116), and a monitor or screen (e.g., such as screen 118) for displaying thickness values.

In operation, referring to FIGS. 1 and 2 for this example embodiment, a user (e.g., test performer, etc.) can perform a calibration procedure for system 100 and test arrangement 200, by placing test probe 202 on, or in close proximity to, a standard part (or other suitable test base structure) that has been coated with an anti-tamper coating material having a known composition and thickness, and recording the thickness value(s) displayed by test and measurement display unit 106. If so desired, the user can perform this calibration procedure multiple times with different standard parts, in order to provide a range of standard thickness values. After completing such a calibration procedure, the user can place test probe 202 on, or in close proximity to, an anti-tamper coated part (e.g., part 208) to be tested, and observe the thickness value displayed by test and measurement unit 106. This observed thickness value can be compared with the range of recorded standard thickness values to determine a particular thickness value for the tested portion of the anti-tamper coating material on the tested part.

Additionally, or as an alternative, the user can move or slide test probe 202 across the part as desired, in order to cover multiple locations on the test part (e.g., part 208). The observed thickness values (e.g., displayed by test and measurement display unit 106) for these multiple locations can be compared with a range of recorded standard thickness values from an earlier calibration procedure, in order to assess the uniformity of the anti-tamper coating material on the tested part. As another alternative, in order to determine the uniformity of an anti-tamper coating material on a part, the user can forgo the above-described calibration procedure, move or slide test probe 202 across the part (e.g., part 208), and note any variance(s) in the thickness values displayed by test and measurement unit 106 as test probe 202 is moved across the part (or, for example, as the part is moved relative to the test probe). The magnitude(s) of the measured variance(s) provide an indication (e.g., absolute indication) of the uniformity of the anti-tamper coating on the tested part. Thus, in accordance with principles of the present invention, a system and method are provided for non-destructively determining the thickness and/or uniformity of an anti-tamper coating on a sensitive electronic part.

It is important to note that while the present invention has been described in the context of a fully functioning non-destructive test system, those of ordinary skill in the art will appreciate that the processes of the present invention are capable of being distributed in the form of a computer readable medium of instructions and a variety of forms and that the present invention applies equally regardless of the particular type of signal bearing media actually used to carry out the distribution. Examples of computer readable media include recordable-type media, such as a floppy disk, a hard disk drive, a RAM, CD-ROMs, DVD-ROMs, and transmission-type media, such as digital and analog communications links, wired or wireless communications links using transmission forms, such as, for example, radio frequency and light wave transmissions. The computer readable media may take the form of coded formats that are decoded for actual use in a particular non-destructive test system.

The description of the present invention has been presented for purposes of illustration and description, and is not intended to be exhaustive or limited to the invention in the form disclosed. Many modifications and variations will be apparent to those of ordinary skill in the art. These embodiments were chosen and described in order to best explain the principles of the invention, the practical application, and to enable others of ordinary skill in the art to understand the invention for various embodiments with various modifications as are suited to the particular use contemplated.

What is claimed is:

1. A system for non-destructively determining the thickness of an anti-tamper coating material on a part, comprising:
   a test probe unit, said test probe unit including at least a beta radiation source and a radiation detector arranged proximally to said beta radiation source, said beta radiation source operable to emit radiation directed toward the anti-tamper coating material, and said radiation detector operable to detect at least a portion of said radiation reflected from the anti-tamper coating material and generate a count associated with said at least a portion of said radiation reflected from the anti-tamper coating material;
   a meter unit coupled to said radiation detector, said meter unit operable to generate a first value associated with said count generated by said radiation detector; and
   a conversion unit coupled to said meter unit, said conversion unit operable to convert said first value to a second value associated with a level of thickness of the anti-tamper coating material.

2. The system of claim 1, wherein said radiation comprises beta radiation.

3. The system of claim 1, wherein said radiation reflected from the anti-tamper coating material comprises beta back scatter.

4. The system of claim 1, wherein said radiation detector comprises a Geiger-Muller tube.

5. The system of claim 1, wherein said meter unit comprises a rate meter.

6. The system of claim 1, wherein said first value comprises a number of electrons collected during a predetermined interval of time.

7. The system of claim 1, herein said second value comprises said level of thickness of the anti-tamper coating material.

8. The system of claim 1, farther comprising a display unit coupled to at least one of said radiation detector, meter unit, or conversion unit, said display unit operable to display a thickness value for the anti-tamper coating material.

9. A system for non-destructively determining the thickness of an anti-tamper coating material on a part, comprising:
   means for emitting beta radiation directed toward the anti-tamper coating material;
   means for detecting at least a portion of said beta radiation reflected from the anti-tamper coating material;
   means for generating a count associated with said at least a portion of said beta radiation reflected from the anti-tamper coating material;
   means for generating a first value associated with said count generated by said radiation detector; and
   means for converting said first value to a second value associated with a level of thickness of the anti-tamper coating material.

10. The system of claim 9, farther comprising: means for displaying a thickness value for the anti-tamper coating material.

11. The system of claim 9, wherein said radiation reflected from the anti-tamper coating material comprises beta back scatter.

12. The system of claim 9, wherein said means for emitting radiation comprises a beta radiation source.

13. The system of claim 9, wherein said means for detecting comprises a Geiger-Muller tube.

14. A method for non-destructively determining the thickness of a non-transparent anti-tamper coating material on a part, comprising the steps of:
- emitting beta radiation directed toward the non-transparent anti-tamper coating material;
- detecting at least a portion of said radiation reflected from the non-transparent anti-tamper coating material;
- generating a count associated with said at least a portion of said radiation reflected from the non-transparent anti-tamper coating material;
- generating a first value associated with said count generated by said radiation detector; and
- converting said first value to a second value associated with a level of thickness of the non-transparent anti-tamper coating material.

15. The method of claim 14, wherein said radiation comprises beta radiation.

16. The method of claim 14, wherein said radiation reflected from the anti-tamper coating material comprises beta back scatter.

17. A computer program product, comprising:
- a computer-usable medium having computer-readable code embodied therein for configuring a computer processor, comprising:
- a first executable computer-readable code configured to cause a computer processor to prompt a beta radiation source to emit radiation directed toward an anti-tamper coating material;
- a second executable computer-readable code configured to cause a computer processor to prompt a radiation detector to detect at least a portion of said radiation reflected from the anti-tamper coating material;
- a third executable computer-readable code configured to cause a computer processor to generate a count associated with said at least a portion of said radiation reflected from the anti-tamper coating material;
- a fourth executable computer-readable code configured to cause a computer processor to generate a first value associated with said count generated by said radiation detector;
- and a fifth executable computer-readable code configured to cause a computer processor to convert said first value to a second value associated with a level of thickness of the anti-tamper coating material.

* * * * *